United States Patent [19]
Portman

[11] Patent Number: 6,051,236
[45] Date of Patent: Apr. 18, 2000

[54] COMPOSITION FOR OPTIMIZING MUSCLE PERFORMANCE DURING EXERCISE

[75] Inventor: Robert Portman, Woodbridge, N.J.

[73] Assignee: Pacifichealth Laboratories, Inc., Woodbridge, N.J.

[21] Appl. No.: 09/190,885

[22] Filed: Nov. 12, 1998

[51] Int. Cl.[7] .................. A61K 31/41; A61K 31/195; A61K 35/78; A61K 33/42; A61K 33/14; A61K 31/70; A61K 31/59

[52] U.S. Cl. .................. 424/195.1; 424/601; 424/678; 424/680; 514/23; 514/168; 514/363; 514/561; 514/562; 514/565; 514/617; 514/643; 514/646

[58] Field of Search .................. 424/601, 678, 424/680, 195.1; 514/23, 168, 363, 561, 562, 565, 617, 643, 646

[56] References Cited

U.S. PATENT DOCUMENTS

| | | | |
|---|---|---|---|
| 4,871,550 | 10/1989 | Millman | 424/601 |
| 5,114,723 | 5/1992 | Stray-Gundersen | 426/74 |
| 5,397,786 | 3/1995 | Simone | 514/300 |
| 5,576,351 | 11/1996 | Yoshimura et al. | 514/565 |

*Primary Examiner*—Raymond Henley, III
*Attorney, Agent, or Firm*—Ezra Sutton

[57] ABSTRACT

A nutritional composition in a dry powder form for optimizing muscle performance during exercise and for enhancing muscle cell repair and recovery following the cessation of exercise. The dry nutritional composition includes carbohydrates and proteins in a ratio in the range of 2.8 to 4.2 parts of the carbohydrates to 1.0 part of the proteins, wherein the carbohydrates are used for providing energy during exercise and the proteins are used for stimulating the release of insulin to the muscle cells during exercise and for repairing muscle cells after exercise. The dry nutritional composition further includes glutamine for reducing muscle stress by stimulating the immune system and for stimulating muscle cell recovery after exercise; arginine for stimulating the release of insulin within the muscle cells in order to facilitate the transport of glucose into the muscle cells during exercise and for the synthesis of glucose into glycogen; vitamin C for use as an anti-oxidant for preventing free radical formation during exercise and for protecting muscle cell integrity during exercise; and vitamin E for use as an anti-oxidant for preventing free radical formation during exercise and for protecting muscle cell integrity during exercise. Additionally, the dry nutritional composition also includes one or more electrolytes for replenishing electrolytes lost during exercise and for facilitating intestinal reabsorption of fluids, and for facilitating energy dependent processes; and an herbal compound being ciwujia for enhancing the immune system, reducing muscle stress, and decreasing heart rate during exercise.

77 Claims, 5 Drawing Sheets

EFFECT ON MEAN EXERCISE PERFORMANCE

*NUTRITIONAL DRINK COMPOSITION OF THE PRESENT INVENTION

EFFECTS ON RATINGS OF PERCEIVED EXERTION

*NUTRITIONAL DRINK COMPOSITION OF THE PRESENT INVENTION

COMPOSITION FOR OPTIMIZING MUSCLE PERFORMANCE DURING EXERCISE

FIELD OF THE INVENTION

The present invention relates to a nutritional composition for optimizing muscle performance during exercise and for enhancing muscle cell repair and recovery following the cessation of exercise. More particularly, the nutritional composition includes carbohydrates to replenish muscle glycogen, proteins to stimulate insulin and repair muscle protein damaged as a consequence of exercise, glutamine for repairing muscle cells and reducing muscle stress, arginine for stimulating the release of insulin, vitamins C and E for reducing free radical buildup, electrolytes for replenishing electrolytes and water lost during exercise, and ciwujia for enhancing endurance and reducing muscle stress.

BACKGROUND OF THE INVENTION

Over the last 20 years, research on exercise performance has focused on two factors, rehydration and carbohydrate supplementation. Research studies conducted over the past 7 years have significantly advanced our understanding of muscle exercise and muscle physiology and have identified additional factors that influence muscle performance.

This research has shown that:

1. Insulin is essential in the post exercise recovery process in replenishing glycogen and in the rebuilding and repair of muscle protein;
2. Protein and specific amino acids can stimulate the insulin response thereby speeding muscle recovery;
3. Free radicals play an important role in exercise induced muscle damage;
4. Anti-oxidants, by reducing oxidative stress, reduce muscle damage and help maintain cell integrity; and
5. Amino acids and certain natural supplements can help minimize muscle stress.

It has been long desirable to speed muscle recovery following exercise. Researchers have identified that optimal muscle recovery depends on four factors:

1. Restoration of fluid (hydration) and electrolytes;
2. Replenishment of muscle glycogen rapidly;
3. Reduction of oxidative and muscle stress; and
4. Rebuilding and repair of muscle protein damaged during exercise.

To date, nutritional intervention to achieve maximum muscle recovery has been primarily directed toward restoration of fluid and electrolytes levels or the replenishment of muscle glycogen stores following exercise.

Replenishment of fluid and electrolytes is the most important of the four factors necessary to achieve rapid muscle recovery post exercise. Researchers have shown that addition of electrolytes to water consumed orally can increase hydration rates by accelerating gastric emptying. After consumption, an electrolyte/water drink will immediately enter the stomach. Minimal absorption of water and electrolytes take place in the stomach. The absorption occurs only after the passage of water and electrolytes into the intestine. The stomach or gastric emptying rate is the essential limiting factor for the rapid replacement of fluids into the body.

The second most important factor is the replenishment of muscle glycogen stores depleted during exercise. Researchers have shown muscle glycogen replenishment post exercise depends on three factors:

1. An adequate source of carbohydrate (approximately 0.7–1.0 gm/kg body weight). The carbohydrate source should be composed primarily of low glycemic index sugars.
2. Stimulation of insulin, a hormone responsible for the transport of glucose into the muscle cell where it becomes a substrate for the synthesis of glycogen, as well as for the stimulation of the enzyme, glycogen synthetase.
3. Timing of the carbohydrate replenishment. The enzyme responsible for converting glucose into glycogen, glycogen synthetase, is maximally stimulated up to 2 hours post exercise.

Addition of protein and arginine to a carbohydrate mixture has been shown to stimulate insulin release, thereby facilitating glucose transport into the muscle cell and stimulating glycogen synthesis. Protein also provides another benefit in the post exercise recovery process by rebuilding muscle cells damaged during exercise.

Although restoration of fluid and electrolytes, glycogen replenishment and rebuilding of protein are three essential factors in achieving optimal muscle recovery, they can cancel each other out physiologically. When protein is added to a recovery drink, it also stimulates a gastric peptide called cholecystokinin (CCK). Fat also stimulates CCK release. CCK has been shown to slow gastric emptying. Therefore, the addition of protein which increases glycogen replenishment and helps rebuild muscle cells after exercise has the negative action of slowing gastric emptying. Slowing gastric emptying slows the replenishment of fluid and electrolytes lost during exercise. Since hydration and electrolyte replenishment post exercise are the most important factors in the post recovery process, any interference will diminish the muscles capacity to recover following cessation of exercise.

The fourth factor essential to muscle recovery is the reduction of oxidative and muscle stress which occur as a normal consequence of increased muscle activity. Increased muscle activity results in the formation of free radicals and release of cortisol, a catabolic hormone responsible for breaking down protein for use as energy. Researchers have reported that addition of anti-oxidants such as vitamin E and vitamin C can reduce the formation of free radicals. Exercise has been shown to place stress on the body's immune system which can further compromise the post recovery process. The amino acid glutamine and the herb ciwujia have been shown to stimulate the immune system. In addition, ciwujia has been shown to reduce exercise induced stress by lowering heart rate.

When the muscle is damaged there is a leakage of an enzyme called creatine kinase (CK) from the muscle cell into the blood. Increased blood levels of the enzyme CK is a measurement of post exercise muscle damage. Peak CK levels are usually reached 24 hours after the cessation of exercise.

There is a definite need in the art for a nutritional intervention composition that will facilitate muscle recovery post exercise by addressing the four key factors above and without the limitations of existing products. It is the object of this invention to provide a safe, nutritional intervention product that will facilitate muscle recovery both during and after the cessation of exercise.

DESCRIPTION OF THE PRIOR ART

Products to enhance stamina and performance which are natural herbal products or synthetically made products having various organic structures and metabolic functions have been disclosed in the prior art. For example, U.S. Pat. No. 5,504,072 to SCHMIDL et al discloses an enteral nutritional composition having a balanced amino acid profile to help patients during recovery. The nutritional composition includes carbohydrates, proteins, glutamine, arginine, vitamins C and E, and electrolytes.

U.S. Pat. No. 5,576,351 to YOSHIMURA et al discloses compositions supplemented with arginine as an immunostimulator for enteral administration to human patients for treating an impaired immune response. The composition includes carbohydrate, protein, glutamine, vitamins and electrolytes.

U.S. Pat. No. 4,871,550 to MILLMAN discloses a nutrient composition for athletes containing amino acids, carbohydrates, vitamins, minerals, trace elements, electrolytes and flavoring aids.

U.S. Pat. Nos. 5,114,723 and 5,032,411 to Stray-Gundersen disclose beverage compositions for human consumption containing vitamins, electrolytes, carbohydrates and nutrient minerals.

U.S. Pat. No. 5,397,786 to SIMONE discloses a rehydration drink for athletes having a composition containing carbohydrates, electrolytes, ammonia neutralizers, energy enhancers (vitamins), amino acids, antioxidants, membrane stabilizers and neuromuscular enhancers.

None of the prior art patents disclose the nutritional composition of the present invention for enhancing endurance, performance and for optimizing muscle recovery following exercise.

Ciwujia has been shown to stimulate the immune system to improve endurance, to reduce heart rate during exercise and to have a carbohydrate sparing effect during exercise. Previously published literature has shown that ciwujia is an exceedingly safe natural product. Ciwujia has been administered to human beings in doses of 3–27 gm/day without any reported side effects. In addition, ciwujia has been administered to laboratory animals at 60 to 200 times the recommended human dose without producing any abnormalities or untoward effects.

Accordingly, it is an object of the present invention to provide a nutritional intervention composition for optimizing muscle performance during exercise and for enhancing muscle cell recovery following the cessation of exercise.

Another object of the present invention is to provide a nutritional intervention composition that restores fluid and electrolytes, replenishes glycogen stores in the muscle, reduces oxidative and muscle stress, and prevents muscle protein breakdown and repairs muscle damaged as a result of exercise.

Another object of the present invention is to provide a nutritional intervention composition that contains carbohydrate and protein in a ratio (Optimum Recovery Ratio) sufficient to stimulate glucose transport, glycogen synthesis and repair of muscle without negatively impacting the critical rehydration process post exercise.

Another object of the present invention is to provide a nutritional intervention composition that enhances muscle performance and endurance because it facilitates the transport of glucose into the muscle cell and stimulates the synthesis of glucose into glycogen.

Another object of the present invention is to provide a nutritional intervention composition that restores fluid and electrolyte levels that are depleted during exercise.

Another object of the present invention is to provide a nutritional intervention composition that reduces muscle and cardiac stress during exercise.

Another object of the present invention is to provide a nutritional intervention composition that reduces oxidative stress by preventing the buildup of free radicals that form as a consequence of exercise.

Another object of the present invention is to provide a nutritional intervention composition that protects against muscle damage that occurs as a consequence of exercise.

Another object of the present invention is to provide a nutritional intervention composition that rebuilds muscle protein damaged during exercise and prevents the breakdown of muscle protein for use as energy.

Another object of the present invention is to provide a nutritional intervention composition that stimulates insulin levels post exercise thereby facilitating the transport of glucose into the muscle and the restoration of glycogen stores and the transport of amino acids into the muscle cell.

Another object of the present invention is to provide a nutritional intervention composition that contains optimum levels of natural ingredients to deliver physiological benefits which will extend performance and endurance during exercise, and also reduce muscle soreness and speed recovery after exercise.

A further object of the present invention is to provide a nutritional intervention composition made into a liquid drink, a liquid concentrate, a reconstituted powder, a nutrition bar that is pleasant tasting and can be mass produced in an automated and economical manner and is readily available to the consumer.

SUMMARY OF THE INVENTION

The present invention provides for a nutritional composition in a dry powder form for optimizing muscle performance during exercise and for enhancing muscle cell repair and recovery following the cessation of exercise.

The dry nutritional composition includes carbohydrates and proteins in a ratio in the range of 2.8 to 4.2 parts of the carbohydrates to 1.0 part of the proteins, wherein the carbohydrates are used for providing energy during exercise and the proteins are used for stimulating the release of insulin to the muscle cells during exercise and for repairing muscle protein damaged during exercise.

One or more carbohydrates are sugars in the range of 68.00% to 88.00% by weight of the dry composition; wherein one or more of the carbohydrates are high glycemic sugars in the range of 50.00% to 70.0% by weight of the dry composition; and wherein one or more of the carbohydrates are low glycemic sugars in the range of 8.00% to 20.00% by weight of the dry composition. One or more proteins are in the range of 17.00% to 22.00% by weight of the dry composition. The dry nutritional composition further includes a first amino acid being glutamine in the range of 0.50% to 2.00% by weight of the dry composition for reducing muscle stress and for stimulating muscle cell recovery after exercise; a second amino acid being arginine in the range of 1.00% to 3.00% by weight of the dry composition for stimulating the release of insulin within the muscle cells in order to facilitate the transport of glucose into the muscle cells during exercise and for the synthesis of glucose into glycogen; a first vitamin compound being vitamin C in the range of 0.50% to 2.00% by weight of the dry composition for use as an anti-oxidant for preventing free radical formation during exercise and for protecting muscle cell integrity during exercise; and a second vitamin compound being vitamin E in the range of 0.50% to 2.00% by weight of the dry composition for use as an anti-oxidant for preventing free radical formation during exercise and for protecting muscle cell integrity during exercise.

The dry nutritional composition also includes a first electrolyte ion being sodium ($Na^+$) compounds in the range of 0.10% to 2.00% by weight of the dry composition for replenishing electrolytes lost during exercise and for facilitating intestinal reabsorption of fluids; a second electrolyte ion being potassium ($K^+$) compounds in the range of 0.10% to 2.00% by weight of the dry composition for replenishing electrolytes lost during exercise and for facilitating intestinal reabsorption of fluids; and a third electrolyte ion being magnesium ($Mg^{+2}$) compounds in the range of 0.10% to 2.00% by weight of the dry composition for replenishing electrolytes lost during exercise and for facilitating energy dependent processes.

Additionally, the dry nutritional composition includes an herbal compound being ciwujia in the range of 0.50% to 3.00% by weight of the dry composition for enhancing the immune system, reducing muscle stress by decreasing heart rate during exercise; and one or more branched-chain amino acids consisting of leucine, isoleucine, and valine amino acids in the range of 2.00% to 5.00% by weight of the dry composition for providing energy during exercise and for repairing muscle cell damage after exercise.

BRIEF DESCRIPTION OF THE DRAWINGS

Further objects, features, and advantages of the present invention will become apparent upon the consideration of the following detailed description of the presently-preferred embodiment when taken in conjunction with the accompanying drawings, wherein.

DETAILED DESCRIPTION OF THE PREFERRED AND ALTERNATE EMBODIMENTS

Figure 1:
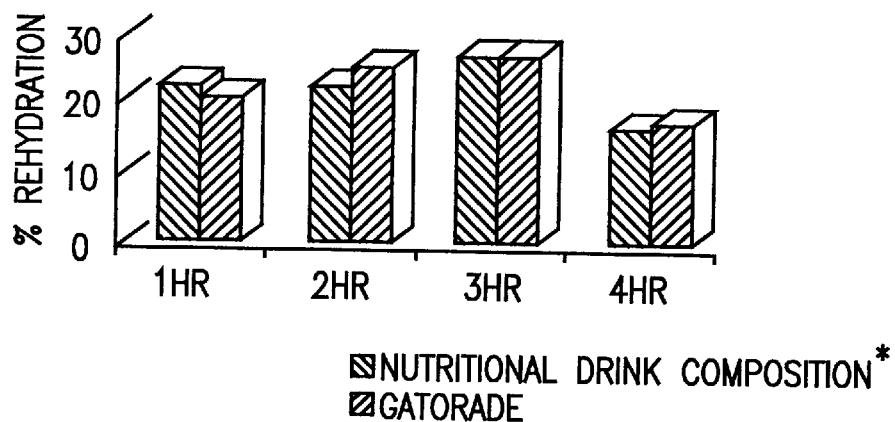
FIG. 1 is a graph showing the comparison of rehydration rates between the nutritional drink composition of the present invention versus the Gatorade™ drink.
Figure 2:
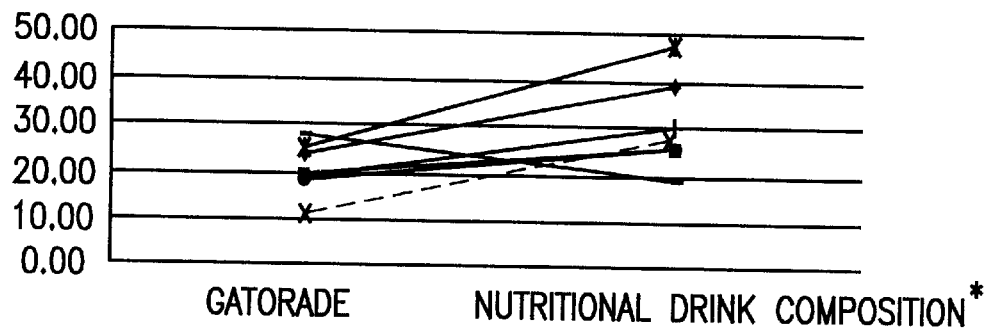
FIG. 2 is a graph showing the effect on exercise performance by individual subject of the nutritional drink composition of the present invention versus the Gatorade™ drink.
Figure 3:
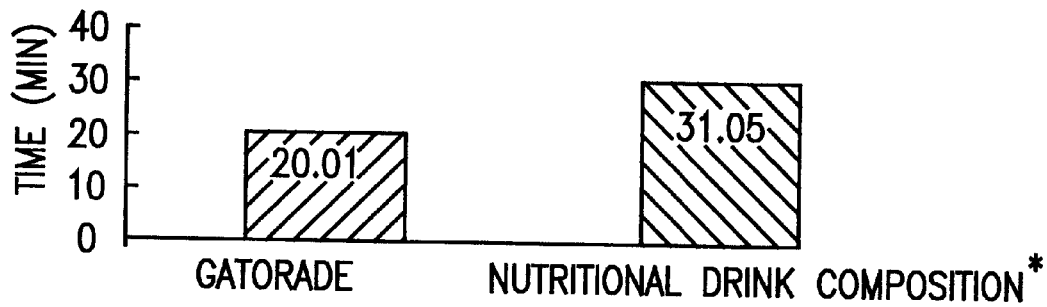
FIG. 3 is a graph showing the effect on mean exercise performance for the nutritional drink composition of the present invention versus the Gatorade™ drink.
Figure 4:
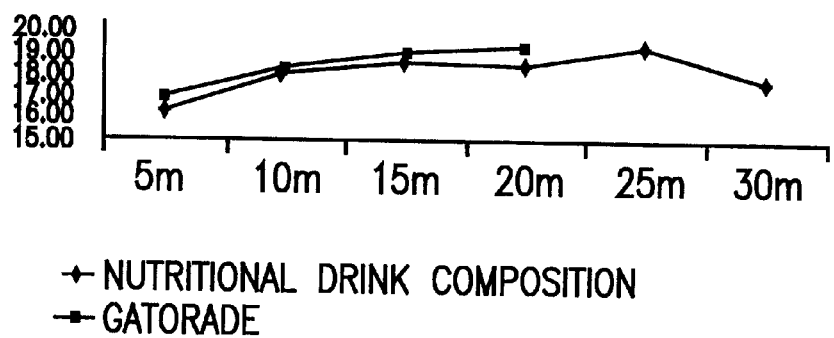
FIG. 4 is a graph showing the effect on ratings of perceived exertion for the nutritional drink composition of the present invention versus the Gatorade™ drink.

The nutritional composition of the preferred and alternate embodiments of the present invention are in a dry form, a liquid drink, an energy bar or in a gelatin format. The nutritional composition is used for optimizing muscle performance during exercise and for enhancing muscle cell repair following the cessation of exercise. The nutritional drink composition of the alternate embodiment is represented in FIGS. 1 through 9 of the drawings in which various performance measurements, levels and indicators are graphed to compare the nutritional drink composition of the present invention versus the Gatorade™ drink. In the present invention, the preferred and alternate embodiments of the nutritional composition are as follows for a dry composition and liquid drink composition:

TABLE A

| | The % Component Compound By Weight | |
|---|---|---|
| Component Compound in a dry powder form | Overall Range | Preferred Range |
| I. Carbohydrates such as sugars in the form of high glycemic sugars and low glycemic sugars | 66% to 88% | 70% to 82% |
| A. High glycemic sugars selected from the groups consisting of aldohexoses, disaccharides and polysaccharides such sugars being glucose, glucose polymers, dextrose, maltose, maltodextrins, maltotriose, lactose, galactose, sucrose, corn syrup, high fructose corn syrup, honey, maple syrup, molasses, beet sugar, cane sugar, and sucanat | 50% to 70% | 60% to 65% |
| B. Low glycemic sugars selected from the group consisting ketohexoses such sugars being arabinose, ribose, xylose, fructose, levulose, psicose, sorbose, tagatose and sorbitol | 8% to 20% | 9% to 15% |
| II. Proteins such as calcium caseinate, whey protein concentrate, whey protein isolate, soy protein, casein hydrolyzate, meat protein concentrate and yeast concentrate | 17% to 22% | 19% to 21% |
| III. A first amino acid being glutamine | 0.5% to 1% | 1% to 1.95% |
| IV. A second amino acid being arginine | 1% to 3% | 1.75% to 2.5% |
| V. A first vitamin being Vitamin C | ½% to 2% | 0.6% to 1% |

TABLE A-continued

| Component Compound in a dry powder form | Overall Range | Preferred Range |
|---|---|---|
| VI. A second vitamin being Vitamin E | ½% to 2% | 0.8% to 1.05% |
| VII. A first electrolyte being sodium compounds such as sodium chloride, sodium acetate, acidic sodium citrate, acidic sodium phosphate, sodium amino salicylate, sodium bicarbonate, sodium bromide, sodium citrate, sodium lactate, sodium phosphate, sodium salicylate, anhydrous sodium sulphate, sodium sulphate, sodium tartrate, sodium benzoate, sodium selenite and sodium molybdate | 0.1% to 2% | 0.5% to 1% |
| VIII. A second electrolyte being potassium compounds such as potassium chloride, potassium acetate, potassium bicarbonate, potassium bromide, potassium citrate, potassium-D-gluconate, monobasic potassium phosphate, potassium tartrate, potassium sorbate and potassium iodide | 0.1% to 2% | 0.14% to 1.5% |
| IX. A third electrolyte being magnesium compounds such as magnesium chloride, magnesium oxide, magnesium sulphate, magnesium carbonate, magnesium aspartate and magnesium silicate | 0.1% to 2% | 0.5% to 1.5% |
| X. A herbal compound being ciwujia | 1/2% to 3% | 0.8% to 2% |
| XI. Branched-chain amino acids being leucine, isoleucine and valine | 2% to 5% | 3% to 4% |
| XII. A diluent in the form of water or juice | 0% | 0% |
| XIII. A flavor component consisting of water soluble natural or artificial extracts | 0.10% to 2% | 0.25% to 1% |
| XIV. A colorant component consisting of natural or artificial water soluble dyes | 0.10% to 2% | 0.125% to 1% |

TABLE B

| Component Compound in a liquid drink form | Overall Range | Preferred Range |
|---|---|---|
| I. Carbohydrates such as sugars in the form of high glycemic sugars and low glycemic sugars | 11% to 15% | 12% to 14% |
| A. High glycemic sugars selected from the groups consisting of aldohexoses, disaccharides and polysaccharides such sugars being glucose, glucose polymers, dextrose, maltose, maltodextrins, maltotriose, lactose, galactose, sucrose, corn syrup, high fructose corn syrup, honey, maple syrup, molasses, beet sugar, cane sugar, and sucanat | 7% to 14% | 10% to 12% |
| B. Low glycemic sugars selected from the group consisting ketohexoses such sugars being arabinose, ribose, xylose, fructose, levulose, psicose, sorbose, tagatose and sorbitol | 1% to 3½% | 1.65% to 2.5% |
| II. Proteins such as calcium caseinate, whey protein concentrate, whey protein isolate, soy protein, casein hydrolyzate, meat protein concentrate and yeast concentrate | 3% to 4% | 3.65% to 3.85% |
| III. A first amino acid being glutamine | 0.08% to 0.4% | 0.10% to 0.35% |
| IV. A second amino acid being arginine | 0.2% to 0.6% | 0.3% to 0.45% |
| V. A first vitamin being Vitamin C | 0.05% to 0.6% | 0.1% to 0.4% |

TABLE B-continued

| Component Compound in a liquid drink form | Overall Range | Preferred Range |
|---|---|---|
| VI. A second vitamin being Vitamin E | 0.10% to 0.6% | 0.15% to 0.4% |
| VII. A first electrolyte being sodium compounds such as sodium chloride, sodium acetate, acidic sodium citrate, acidic sodium phosphate, sodium amino salicylate, sodium bicarbonate, sodium bromide, sodium citrate, sodium lactate, sodium phosphate, sodium salicylate, anhydrous sodium sulphate, sodium sulphate, sodium tartrate, sodium benzoate, sodium selenite and sodium molybdate | 0.05% to 0.6% | 0.1% to 0.4% |
| VIII. A second electrolyte being potassium compounds such as potassium chloride, potassium acetate, potassium bicarbonate, potassium bromide, potassium citrate, potassium-D-gluconate, monobasic potassium phosphate, potassium tartrate, potassium sorbate and potassium iodide | 0.05% to 0.6% | 0.2% to 0.4% |
| IX. A third electrolyte being magnesium compounds such as magnesium chloride, magnesium oxide, magnesium sulphate, magnesium carbonate, magnesium aspartate and magnesium silicate | 0.05% to 2% | 0.09% to 0.4% |
| X. A herbal compound being ciwujia | 0.05% to 0.6% | 0.14% to 0.4% |
| XI. Branched-chain amino acids being leucine, isoleucine and valine | 2% to 5% | 0.6% to 0.75% |
| XII. A diluent in the form of water or juice | 80% to 85% | 82% to 84% |
| XIII. A flavor component consisting of water soluble natural or artificial extracts | 0.01% to 0.5% | 0.04% to 0.1% |
| XIV. A colorant component consisting of natural or artificial water soluble dyes | 0.01% to 0.5% | 0.02% to 0.1% |

TABLE C

| Component Compound | Grams | Dry | Liquid |
|---|---|---|---|
| Glucose | 22.99 | 30.99% | 5.55% |
| Maltodextrin | 23.47 | 31.64% | 5.66% |
| Fructose | 7.90 | 9.44% | 1.69% |
| Whey Protein Concentrate | 15.31 | 20.64% | 3.69% |
| Vitamin E Acetate | 0.80 | 1.08% | 0.19% |
| Glutamine | 0.42 | 0.57% | 0.10% |
| Ciwujia | 0.60 | 0.81% | 0.14% |
| Ascorbic Acid | 0.47 | 0.63% | 0.11% |
| Magnesium Oxide (MgO) | 0.40 | 0.54% | 0.09% |
| Potassium Phosphate | 0.10 | 0.14% | 0.02% |
| Arginine | 1.42 | 1.91% | 0.34% |
| Sodium Chloride (NaCl) | 0.45 | 0.61% | 0.10% |
| Flavoring Agent | 0.19 | 0.25% | 0.04% |
| Colorant | 0.10 | 0.13% | 0.02% |
| Citric Acid | 0.46 | 0.62% | 0.11% |
| Ingredient Subtotal | 74.18 | | 17.9% |
| Water (H$_2$O) | 340.2 | 0% | 82.1% |
| | 414.38 | 100.0% | 100.0% |

TABLE D

| | Grams | |
|---|---|---|
| Maltodextrin | 22.99 | |
| Glucose | 23.47 | |
| Fructose | 7.00 | |
| Carbohydrate Total | 53.46 | |
| Whey protein concentrate | 11.79 | |
| Added Glutamine | 0.42 | |
| Added Arginine | 1.42 | |
| Protein Total | 13.63 | |
| Carbohydrate/Protein Ratio | 3.92 to 1.00 | |
| Glutamic acid in whey protein concentrate | 1.02 | |
| Added Glutamine | 0.42 | |
| Glutamine plus glutamic acid Total | 2.54 | |
| Arginine in whey protein concentrate | 0.31 | |
| Added Arginine | 1.42 | |
| Arginine Total | 1.73 | |
| Leucine 11.9/100 g whey protein concentrate | 1.40 | |
| Isoleucine 5.4/100 g whey protein concentrate | 0.64 | |
| Valine 5.1/100 g whey protein concentrate | 0.60 | |
| Branched Chain Amino Acid Total | 2.64 | |
| Vitamin E | 400 | IU |
| Ascorbic Acid | 466 | mg |
| Ciwujia | 600 | mg |
| Magnesium Oxide | 400 | mg |

TABLE D-continued

| | Grams |
|---|---|
| Potassium Phosphate | 100 mg |
| Sodium Chloride | 450 mg |

PREFERRED EMBODIMENT

The nutritional composition for nutritional intervention for achieving maximum muscle recovery during and after exercising includes nutritional agents being carbohydrates, proteins, branched-chain amino acids, amino acids, vitamins, electrolytes, herbal compounds, flavoring agents, coloring agents and diluents. Carbohydrates include sugars for use as an energy source and the replenishment of muscle glycogen stores. These sugars include high glycemic sugars and low glycemic sugars. High glycemic sugars are selected from the group consisting of aldohexoses, disaccharides and polysaccharides such sugars being glucose, glucose polymers, dextrose, maltose, maltodextrins, maltotriose, lactose, galactose, sucrose, corn syrup, high fructose corn syrup, honey, maple syrup, molasses, beet sugar, cane sugar, and sucanat. Low glycemic sugars is are selected from the group consisting of ketohexoses such sugars being arabinose, ribose, xylose, fructose, levulose, psicose, sorbose, tagatose and sorbitol. Total carbohydrates are in the overall range of 66.00% to 88.00% by weight of the dry nutritional composition having a preferred range of 70.00% to 82.00% by weight of the dry nutritional composition. High glycemic sugars are in the overall range of 50.00% to 70.00% by weight of the dry nutritional composition having a preferred range of 60.00% to 65.00%. Low glycemic sugars are in the overall range of 8.00% to 20.00% by weight of the dry nutritional composition having a preferred range of 9.00% to 15.00% by weight of the dry nutritional composition.

One or more protein compounds are used in the forming of the dry nutritional composition. These proteins are used as a source of stimulation in the release of insulin during exercise and for the repair of muscle protein damage after exercising has been completed. Protein sources are selected from the group consisting of calcium caseinate, whey protein concentrate, whey protein isolate, soy protein, casein hydrolyzate, meat protein concentrate and yeast concentrate. Total proteins are in the overall range of 17.00% to 22.00% by weight of the dry nutritional composition having a preferred range of 19.00% to 21.00% by weight of the dry nutritional composition.

Figure 6:
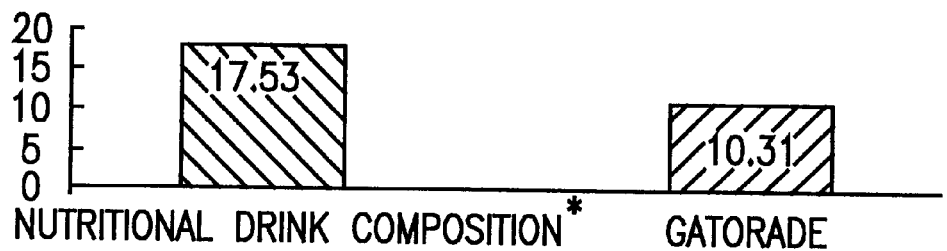
FIG. 6 is a graph showing the effect on mean insulin levels for the nutritional drink composition of the present invention versus the Gatorade™ drink.
Figure 7:
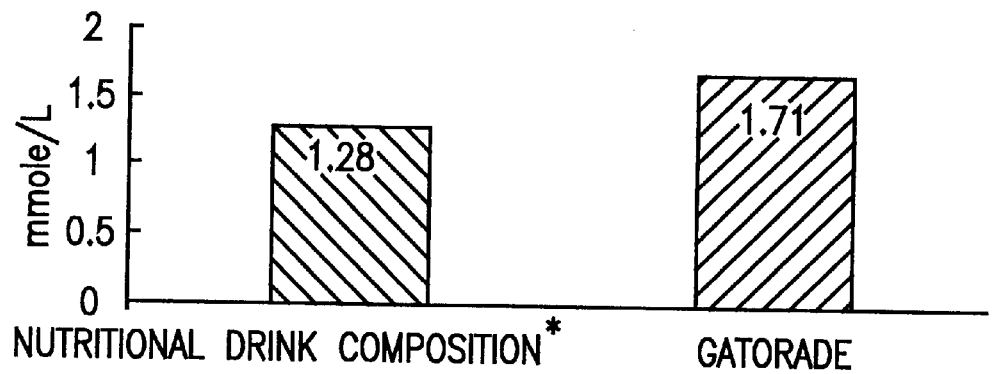
FIG. 7 is a graph showing the effect on mean lactate levels for the nutritional drink composition of the present invention versus the Gartorade™ drink.

Carbohydrates and proteins are in a ratio in the range of 2.8 to 4.2 parts of the carbohydrates to 1.0 part of the proteins; such that the carbohydrates are used for providing energy during exercise and the proteins are used for stimulating the release of insulin to the muscle cells during exercise and for repairing muscle cells after exercise. Our research studies have shown that protein added to carbohydrate in the ratio of one part protein to 2.8 to 4.2 parts of carbohydrate increases the insulin level almost by 40% (See FIG. 6). Thus, it would appear the sports drink of the present invention with protein and carbohydrate in aforementioned ratios does offer an advantage in the recovery process, as shown in FIG. 7. However, more protein can be less effective, as too much protein can have an adverse effect on gastric emptying. Protein stimulates a peptide called cholecystokinin (CCK) which slows stomach emptying. In the recovery phase, decreased gastric emptying can slow the critical process by which fluid and electrolytes are replenished. CCK is also stimulated by fat which points up the negative in including fat in a recovery drink or immediate post exercise meal. The challenge is how to gain the benefits of protein without the negative effect on gastric emptying. Our research has shown that there is a critical ratio of carbohydrate to protein, termed as the Optimum Recovery Ratio or $OR^2$. When the aforementioned ratio of carbohydrate to protein is 4 (or example 56 grams of carbohydrate and 14 grams of protein) the insulin stimulating action of protein does not appear to interfere with the essential rehydration phase as shown by our research (See FIG. 1).

Single strand and branched-chain amino acids are used for reducing muscle stress during exercise, for stimulating muscle cell recovery after exercise, for stimulating the release of insulin within the muscle cells in order to facilitate the transport of glucose into the muscle cells during exercise, to stimulate the synthesis of glucose into glycogen, for providing energy during exercise and for repairing muscle cell damage after the cessation of exercise and for stimulating the immune system. Single strand amino acids used for the nutritional composition include glutamine and arginine. Branched-chain amino acids used for the nutritional composition include leucine, isoleucine and valine.

In particular, a first amino acid used is glutamine in the overall range of 0.50% to 2.00% by weight of the dry nutritional composition having a preferred range of 1.00% to 1.95% by weight of the dry nutritional composition. Glutamine is used for reducing muscle stress by stimulating the immune system during exercise and for stimulating muscle cell recovery after exercise. A second amino acid used is arginine in the overall range of 1.00% to 3.00% by weight of the dry nutritional composition having a preferred range of 1.75% to 2.50% by weight of the dry nutritional composition. Arginine is used for stimulating the release of insulin within the muscle cells in order to facilitate the transport of glucose into the muscle cells during exercise and stimulate the synthesis of glucose into glycogen.

One or more branched-chain amino acids include leucine, isoleucine and valine amino acids in the overall range of 2.00% to 5.00% by weight of the dry nutritional composition having a preferred range of 3.00% to 4.00% by weight of the dry nutritional composition. The branched-chain amino acids are used for providing energy to the user during exercise and for repairing muscle cell damage after exercise.

Vitamin compounds are used as anti-oxidants for preventing free radical formation during exercise and for protecting muscle cell integrity during exercise. Vitamin compounds used for the nutritional composition include Vitamin C in the form of ascorbic acid, Vitamin E in the form of Vitamin E acetate, Vitamin B12, beta-carotene and combinations thereof.

In particular, a first vitamin compound used is Vitamin C in the overall range of 0.50% to 2.00% by weight of the dry nutritional composition having a preferred range of 0.60% to 1.00% by weight of the dry nutritional composition. A second vitamin compound used is Vitamin E in the overall range of 0.50% to 2.00% by weight of the dry nutritional composition having a preferred range of 0.80% to 1.05% by weight of the dry nutritional composition.

Electrolytes being sodium, potassium and magnesium compounds are used within the nutritional composition for replenishing the electrolytes lost during exercise, for facilitating intestinal reabsorption of fluids, and for facilitating energy dependent processes. A first electrolyte being sodium compounds include sodium chloride, sodium acetate, acidic sodium citrate, acidic sodium phosphate, sodium amino salicylate, sodium bicarbonate, sodium bromide, sodium citrate, sodium lactate, sodium phosphate, sodium salicylate, anhydrous sodium sulphate, sodium sulphate, sodium tartrate, sodium benzoate, sodium selenite and sodium molybdate. A second electrolyte being potassium compounds include potassium chloride, potassium acetate, potassium bicarbonate, potassium bromide, potassium citrate, potassium-D-gluconate, monobasic potassium phosphate, potassium tartrate, potassium sorbate and potassium iodide. A third electrolyte being magnesium compounds include magnesium chloride, magnesium oxide, magnesium sulphate, magnesium carbonate, magnesium aspartate and magnesium silicate. A first electrolyte ion being sodium (Na$^+$) compounds in the overall range of 0.10% to 2.00% by weight of the dry nutritional composition having a preferred range of 0.50% to 1.50% by weight of the dry nutritional composition. A second electrolyte ion being potassium (K$^+$) compounds in the overall range of 0.10% to 2.00% by weight of the dry nutritional composition having a preferred range of 0.14% to 1.50% by weight of the dry nutritional composition. A third electrolyte ion being magnesium (Mg$^{+2}$) compounds in the overall range of 0.10% to 2.00% by weight of the dry nutritional composition having a preferred range of 0.50% to 1.5% by weight of the dry nutritional composition.

Herbal compounds used with the nutritional composition include ciwujia, ginseng, astralagus and cordyceps. These herbal compounds are used for enhancing the immune system, reducing muscle stress, and decreasing heart rate during exercise. The herbal compound ciwujia is in the overall range of 0.5% to 3.0% by weight of the dry nutritional composition having a preferred range of 0.80% to 2.0% by weight of the dry nutritional composition.

Other component constituents of the nutritional composition in dry and liquid form include flavor components and/or colorant components. The flavor component for the nutritional composition of the present invention is defined to impart a particular and characteristic taste and sometimes an aroma to the nutritional composition. The use of a flavor component in the nutritional composition also provides an enhanced aesthetic quality to the nutritional composition which will increase the user's appeal in using the product. The flavor component is selected from the group consisting of water soluble natural or artificial extracts that include apple, banana, cherry, cinnamon, cranberry, grape, honeydew, honey, kiwi, lemon, lime, orange, peach, peppermint, pineapple, raspberry, tangerine, watermelon, wild cherry, and equivalents and combinations thereof, being in the overall range of 0.10% to 2.0% by weight of the dry nutritional composition having a preferred range of 0.25% to 1.00% by weight of the dry nutritional composition.

The colorant component for the nutritional composition of the present invention is defined to impart a characteristic color in conjunction with a particular flavor to the nutritional composition. For example, a yellow color is used for a banana flavor, or a red color for a cherry flavor. The colorant component is selected from the group consisting of water soluble natural or artificial dyes that include FD&C dyes (food, drug and cosmetic use dyes) of blue, green, orange, red, yellow and violet; iron oxide dyes; ultramarine pigments of blue, pink, red and violet; and equivalents thereof; being in the overall range of 0.10% to 2.0% by weight of the dry nutritional composition having a preferred range of 0.125% to 1.0% by weight of the dry nutritional composition. The dyes discussed above are well known, and are commercially available materials, with their chemical structure being described, e.g., in 21 C.F.R. Part 74 (as revised Apr. 1, 1988) and the CTFA Cosmetic Ingredient Handbook, (1988), published by the Cosmetics, Toiletry and Fragrancy Association, Inc.

FIRST ALTERNATE EMBODIMENT

Typically, the dry nutritional composition, as shown in Tables B and C, is mixed with water, such that approximately 74 grams of the dry nutritional composition is dissolved in twelve (12) ounces of water (340.2 grams) in order to provide the nutritional drink composition (approximately 14.6 oz. of the liquid nutritional intervention drink composition is made per 12 oz. of water) for consumption prior to the user doing exercise. Table D shows the dry weight in grams of the constituent compounds of the nutritional composition prior to the dilution of using water.

Total carbohydrates are in the overall range of 11.0% to 15.0% by weight of the nutritional drink composition having a preferred range of 12.0% to 14.0% by weight of the nutritional drink composition. High glycemic sugars are in the overall range of 7.0% to 14.0% by weight of the nutritional drink composition having a preferred range of 10.0% to 12.0% by weight of the nutritional drink composition. Low glycemic sugars are in the overall range of 1.5% to 3.5% by weight of the nutritional drink composition having a preferred range of 1.65% to 2.5% by weight of the nutritional drink composition.

Total proteins are in the overall range of 3.0% to 4.0% by weight of the nutritional drink composition having a preferred range of 3.65% to 3.85% by weight of the nutritional drink composition.

A first amino acid is used being glutamine in the overall range of 0.08% to 0.40% by weight of the liquid nutritional composition having a preferred range of 0.10% to 0.35% by weight of the liquid nutritional composition. A second amino acid is used being arginine in the overall range of 0.20% to 0.60% by weight of the liquid nutritional composition having a preferred range of 0.30% to 0.45% by weight of the liquid nutritional composition.

One or more branched-chain amino acids include leucine, isoleucine and valine amino acids in the overall range of 0.40% to 0.90% by weight of the liquid nutritional composition having a preferred range of 0.60% to 0.75% by weight of the liquid nutritional composition.

In particular, a first vitamin compound used is Vitamin C in the overall range of 0.05% to 0.60% by weight of the liquid nutritional composition having a preferred range of 0.10% to 0.40% by weight of the liquid nutritional composition. A second vitamin compound used is Vitamin E in the overall range of 0.10% to 0.60% by weight of the liquid nutritional composition having a preferred range of 0.15% to 0.40% by weight of the liquid nutritional composition.

A first electrolyte ion being sodium (Na$^+$) compounds in the overall range of 0.05% to 0.60% by weight of the liquid nutritional composition having a preferred range of 0.10% to 0.40% by weight of the liquid nutritional composition. A second electrolyte ion being potassium (K$^+$) compounds in the overall range of 0.005% to 0.60% by weight of the liquid nutritional composition having a preferred range of 0.02% to 0.40% by weight of the liquid nutritional composition. A third electrolyte ion being magnesium (Mg$^{+2}$) compounds in the overall range of 0.05% to 0.60% by weight of the liquid nutritional composition having a preferred range of 0.09% to 0.40% by weight of the liquid nutritional composition.

The herbal compound is ciwujia is in the overall range of 0.05% to 0.6% by weight of the liquid nutritional composition having a preferred range of 0.14% to 0.40% by weight of the liquid nutritional composition.

The diluent is in the form of water or juice in the overall range of 80.00% to 85.00% by weight of the liquid nutritional composition. The preferred range of the diluent is 82.00% to 84.00% by weight of the liquid nutritional composition. Juices used as a diluent are selected from the group consisting of grape juice, apple juice, cranberry juice, orange juice, grapefruit juice, tangerine juice, peach juice, strawberry juice and combinations and equivalents thereof.

The flavor component is in the overall range of 0.01% to 0.50% by weight of the liquid nutritional composition having a preferred range of 0.04% to 0.10% by weight of the liquid nutritional composition.

The colorant component is in the overall range of 0.01% to 0.50% by weight of the liquid nutritional composition having a preferred range of 0.02% to 0.10% by weight of the liquid nutritional composition.

Other embodiments for the nutritional composition include energy bars where the carrier is in the form of chocolate, oats, wheat, peanut butter, semi-dried fruits, grains and combinations thereof; and a gelatin product where the carrier is in the form of gelatin and water.

Two studies were conducted to measure the effect of the nutritional drink composition of the present invention versus the Gatorade™ drink. The object of these studies was to measure a number of performance parameters, the effect of the two drinks on insulin and glucose levels, the buildup of free radicals and the effect on tissue damage that normally results as a consequence of exercise.

Experiment One

This study was conducted with eight male high fit subjects ranging in age from 21–35 years old. The study was a cross over design consisting of three phases, a glycogen depletion phase at which subjects exercised at 75% VO2 max for two hours. This phase also included three sprint phases defined as five minutes at 85% VO2 max. This study protocol insured that there was depletion of glycogen from both muscle and liver stores. The glycogen depletion phase was followed by a four hour recovery phase in which the subjects were weighed to measure hydration loss. Immediately after the glycogen depletion phase and then again at two hours subjects were given 12 ozs. of either of the two performance drinks. Following the recovery phase all subjects performed a performance test in which they exercised at a work load level of 85% VO2 max for as long as the subject could go at that level.

During all three phases of the test, blood was sampled and all exercise parameters measured. The results of this experiment showed the following:

1. The nutritional drink composition of the present invention improved time to exhaustion 11.04±3.54 minutes or a 55.0% increase over the Gatorade™ drink.
2. The nutritional drink composition of the present invention decreased total oxidation activity as measured by diene, triene and T-Bars over the Gatorade™ drink. Diene levels dropped 42% over Gatorade™. In addition there was a drop in triene and T-Bars. The nutritional drink composition of the present invention decreased total oxidative product formation (diene, triene plus T-Bars) almost 70%.
3. The nutritional drink composition of the present invention increased the mean level of insulin by 70% over Gatorade™.
4. The nutritional drink composition of the present invention decreased the mean level of lactate over Gatorade™ immediately following the performance bout.
5. The nutritional drink composition of the present invention decreased heart rate over Gatorade™.
6. The nutritional drink composition of the present invention showed equal hydration efficiency to Gatorade™.
7. The nutritional drink composition of the present invention showed a decreased level of perceived exertion when compared to Gatorade™.
8. The nutritional drink composition of the present invention showed a decrease in lactic acid levels when compared to Gatorade™.

Experiment Two

In this experiment ten well trained triathletes completed two simulated duathalons. The experiment was a cross over design consisting of four phases. In the first phase subjects ran on a treadmill at moderate intensity (75% of their VO2 max) for 45 minutes. This phase also included race surges of 1-minute duration every 15 minutes during the first phase. At the end of the first phase subjects had a 10-minute rest in which they consumed either one of the two performance drinks. In the third phase they cycled for 30 minutes at 75% of their VO2 max. 45 minutes into the running, subjects ingested either of the two performance drinks; and 30 minutes into the cycling phase subjects ingested 6 oz. of either of the two performance drinks. At the end of the cycling phase all subjects underwent a performance bout measuring the time necessary to complete 60,000 joules of work. During this experiment exercise physiology parameters were measured and blood periodically sampled. The results of this experiment showed the following:

1. The nutritional drink composition of the present invention decreased the time necessary to complete the performance bout by 3%.
2. The nutritional drink composition of the present invention decreased heart rate over Gatorade™.
3. The nutritional drink composition of the present invention decreased creatine kinase levels by 36%, 24 hours post exercise.

OPERATION OF THE PRESENT INVENTION

The nutritional composition performance drink of the present invention demonstrates how nutrition can enhance aerobic performance, muscle performance, and recovery. The nutritional composition delivers the following benefits:

1. Improve peak muscle performance and extend endurance (See FIGS. 2, 3, 4 and 7);
2. Produce a faster recovery from exercise by rapidly replenishing depleted muscle glycogen stores (See FIG. 6);
3. Reduce muscle stress and protect the muscle from buildup of free radicals thereby reducing post exercise muscle soreness (See FIGS. 5 and 8); and
4. Help rebuild and repair damaged muscle tissue (See FIG. 9).

The nutritional composition provides a simple framework for the aerobic athlete to optimize muscle performance and speed recovery. The nutritional composition of the present invention operates to:

1. Restore electrolytes and water;
2. Replenish glycogen stores;
3. Reduce muscle and oxidative stress; and
4. Rebuild muscle tissue.

1. Restores Electrolytes and Water

Fluid and electrolyte replenishment is crucial in maintaining cardiac output and regulating body temperature during exercise. Elevations in body temperature can sharply impair performance. Studies have shown that fluid replacement must occur both during and after exercise, as shown in FIG. 6 of the drawings. Electrolytes, now usually added to sports hydration drinks, can accelerate rehydration by speeding intestinal reabsorption of fluids and improve fluid retention.

2. Replenishes Glycogen Stores

Carbohydrate supplementation stimulates insulin, a key element in the glycogen replenishment process, as shown in FIG. 7 of the drawings. Insulin serves two major purposes in the glycogen replenishment process:

1. Facilitates the transport of glucose into the muscle cell; and
2. Stimulates enzymes responsible for the synthesis of glycogen from glucose.

A pre, during and post exercise carbohydrate supplement composed of high Glycemic Index Carbohydrates (such as a glucose sugar) is more rapidly transported into the muscle cell in the critical post recovery period. Enzymes responsible for manufacture of muscle glycogen are maximally stimulated 0–2 hours after exercise. Therefore, it is essential that a carbohydrate supplement be taken in this time frame to optimize recovery.

Protein and arginine, when combined with a carbohydrate supplement, strongly stimulate insulin levels in a synergistic fashion. (As shown in FIG. 7). The ratio of carbohydrate to protein is extremely important to obtain this synergy. The optimum replenishment ratio ($OR^2$) should be 2.8 to 4.2 (two point eight grams to four grams of carbohydrate to one gram of protein.) Our research studies have shown that protein added to carbohydrate in the ratio of one part protein to 2.8 to 4.2 parts of carbohydrate have almost doubled the insulin response. Thus, it would appear the sports drink of the present invention with protein and carbohydrate in aforementioned ratios does offer an advantage in the recovery process, as shown in FIG. 7. However, more protein can be less effective, as too much protein can have an adverse effect on gastric emptying. Protein stimulates a peptide called cholecystokinin (CCK) which slows stomach emptying. In the recovery phase, decreased gastric emptying can slow the critical process by which fluid and electrolytes are replenished. CCK is also stimulated by fat which points up the negative in including fat in a recovery drink or immediate post exercise meal. The challenge is how to gain the benefits of protein without the negative effect on gastric emptying. When the aforementioned $OR^2$ ratio of carbohydrate to protein is 4 (or example 56 grams of carbohydrate and 14 grams of protein) the insulin stimulating action of protein does not appear to interfere with the essential rehydration phase (See FIG. 1). By further stimulating insulin with protein and arginine, muscle glycogen is quickly restored. The result is an improved performance and a faster recovery.

3. Reduces Oxidative/Muscle Stress

Figure 5:
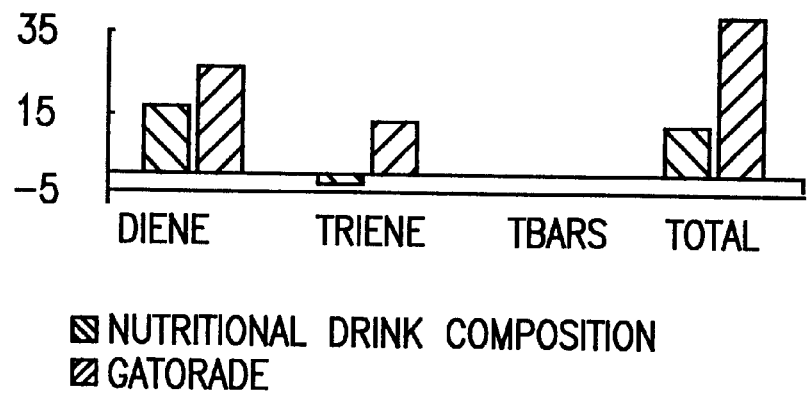
FIG. 5 is a graph showing the effect on free radical formation for the nutritional drink composition of the present invention versus the Gatorade™ drink.

The muscle cell undergoes considerable trauma and muscle stress during exercise. This trauma leads to soreness and rebuilding of muscle post exercise. During exercise there is a buildup of free radicals. Free radicals are largely responsible for damage to the muscle cell membrane. Vitamin C and E are strong anti-oxidants shown to prevent free radical buildup during exercise, as depicted in FIG. 5 of the drawings.

Figure 8:
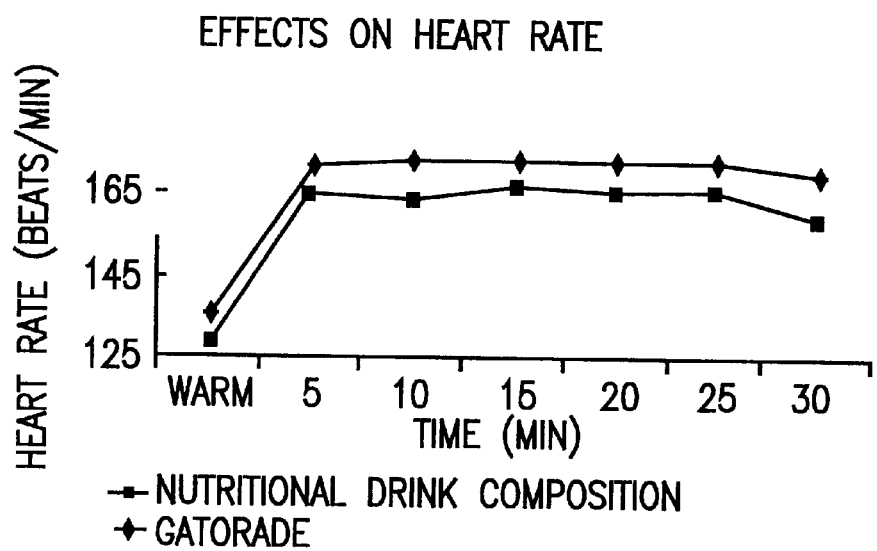
FIG. 8 is a graph showing the effect on heart rate for the nutritional drink composition of the present invention versus the Gatorade™ drink.

A third consequence of hard exercise is an effect on the immune system. The amino acid glutamine has been shown to stimulate the immune system. In addition, the natural herb, ciwujia, bolsters the immune system as well as reduces stress on the heart by lowering heart rate during exercise. This reduces muscle damage and soreness which results in a faster recovery and the ability to maintain a higher training level. (As shown in FIG. 8).

4. Rebuilds Muscle

Exercise increases the stimulation of cortisol, a catabolic hormone that increases the breakdown of protein for energy. Insulin has been shown to blunt the rise in cortisol normally seen after exercise. By stimulating insulin the nutritional drink composition of the present invention blocks the rise in cortisol thereby preventing muscle cell breakdown. Immediately following exercise a rebuilding process is initiated to repair muscle proteins damaged during exercise. Insulin is a strong stimulus of the muscle rebuilding process. Insulin plays a key role in increasing amino acid transport into the muscle and stimulating the cellular machinery that regulates protein synthesis. This interrelationship between glycogen replenishment, insulin, cortisol and muscle rebuilding is an important correlation of the present invention.

A second aspect of the rebuilding process is the need for protein, glutamine and branched-chain amino acids. Protein serves a dual role. It not only stimulates the replenishment of glycogen stores by activating insulin, but also provides the essential building blocks for muscle repair.

Figure 9:
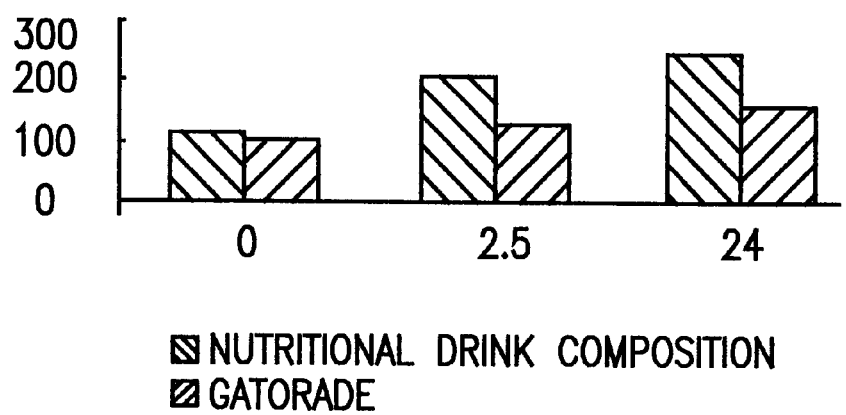
FIG. 9 is a graph showing the effect on creatine kinase levels for the nutritional drink composition of the present invention versus the Gatorade™ drink.

The sports nutrition composition of the present invention operates to:

1. Significantly improve endurance of 66% (See FIGS. 2, 3 and 7); and enhance muscle performance thereby increasing training level (See FIG. 4);
2. Protect the muscle cell from post exercise muscle damage; and reduce muscle damage by reducing the total free radical buildup by 69%, as shown in FIG. 5, thereby reducing muscle cell damage by 40%, as shown in FIG. 9;
3. Generate faster recovery from exercise;
4. Stimulate insulin response thereby speeding the replenishment of muscle glycogen stores; and
5. Facilitate the rebuilding of muscle tissue damaged as a consequent of exercise.

ADVANTAGES OF THE PRESENT INVENTION

Accordingly, an advantage of the present invention is that it provides for a nutritional intervention composition for optimizing muscle performance during exercise and for enhancing muscle cell recovery following the cessation of exercise.

Another advantage of the present invention is that it provides for a nutritional intervention composition that restores fluid and electrolytes, replenishes glycogen stores in the muscle, reduces oxidative and muscle stress, and prevents muscle protein breakdown and repairs muscle damaged as a result of exercise.

Another advantage of the present invention is that it provides for a nutritional intervention composition that contains carbohydrate and protein in a ratio (Optimum Recovery Ratio) sufficient to stimulate glycogen synthesis and repair of muscle without negatively impacting the critical rehydration and glycogen replenishment process post exercise.

Another advantage of the present invention is that it provides for a nutritional intervention composition that enhances muscle performance and endurance because it facilitates the transport of glucose into the muscle cell and the synthesis of glucose into glycogen.

Another advantage of the present invention is that it provides for a nutritional intervention composition that restores fluid and electrolyte levels that are depleted during exercise.

Another advantage of the present invention is that it provides for a nutritional intervention composition that reduces muscle and cardiac stress during exercise.

Another advantage of the present invention is that it provides for a nutritional intervention composition that reduces oxidative stress by preventing the buildup of free radicals that form as a consequence of exercise.

Another advantage of the present invention is that it provides for a nutritional intervention composition that protects against muscle damage that occurs as a consequence of exercise.

Another advantage of the present invention is that it provides for a nutritional intervention composition that rebuilds muscle protein damaged during exercise and reduces the breakdown of muscle protein for use as energy.

Another advantage of the present invention is that it provides for a nutritional intervention composition that stimulates insulin levels post exercise thereby facilitating the transport of glucose into the muscle and the restoration of glycogen stores and the transport of amino acids into the muscle cell.

Another advantage of the present invention is that it provides for a nutritional intervention composition that contains optimum levels of natural ingredients to deliver physiological benefits which will extend performance and endurance during exercise, and also reduce muscle soreness and speed recovery after exercise.

A further advantage of the present invention is that it provides for a nutritional intervention composition made into a liquid drink, a liquid concentrate, a reconstituted powder, a nutrition bar that is pleasant tasting and can be mass produced in an automated and economical manner and is readily available to the consumer.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A nutritional composition in a dry powder form for optimizing muscle performance during exercise and for enhancing muscle cell repair and recovery following the cessation of exercise, comprising:
   a) one or more carbohydrates being sugars in the range of 68.00% to 88.00% by weight of said dry composition for providing energy during exercise; wherein said one or more carbohydrates are high glycemic sugars in the range of 50.00% to 70.0% by weight of said dry composition; and wherein said one or more carbohydrates are low glycemic sugars in the range of 8.00% to 20.00% by weight of said dry composition;
   b) one or more proteins being in the range of 17.00% to 22.00% by weight of said dry composition for stimulating the release of insulin to the muscle cells during exercise and for repairing muscle cells after exercise;
   c) a first amino acid being glutamine in the range of 0.50% to 2.00% by weight of said dry composition for reducing muscle stress by stimulating the immune system and for stimulating muscle cell recovery after exercise;
   d) a second amino acid being arginine in the range of 1.00% to 3.00% by weight of said dry composition for stimulating the release of insulin within the muscle cells in order to facilitate the transport of glucose into the muscle cells during exercise and for the synthesis of glucose into glycogen;
   e) a first vitamin compound being vitamin C in the range of 0.50% to 2.00% by weight of said dry composition for use as an anti-oxidant for preventing free radical formation during exercise and for protecting muscle cell integrity during exercise;
   f) a second vitamin compound being vitamin E in the range of 0.50% to 2.00% by weight of said dry composition for use as an anti-oxidant for preventing free radical formation during exercise and for protecting muscle cell integrity during exercise;
   g) a first electrolyte ion being sodium ($Na^+$) compounds in the range of 0.10% to 2.00% by weight of said dry composition for replenishing electrolytes lost during exercise and for facilitating intestinal reabsorption of fluids;
   h) a second electrolyte ion being potassium ($K^+$) compounds in the range of 0.10% to 2.00% by weight of said dry composition for replenishing electrolytes lost during exercise and for facilitating intestinal reabsorption of fluids;
   i) a third electrolyte ion being magnesium ($Mg^{+2}$) compounds in the range of 0.10% to 2.00% by weight of said dry composition for replenishing electrolytes lost during exercise and for facilitating energy dependent processes;
   j) an herbal compound being ciwujia in the range of 0.50% to 3.00% by weight of said dry composition for enhancing the immune system, reducing muscle stress, and decreasing heart rate during exercise; and
   k) one or more branched-chain amino acids consisting of leucine, isoleucine, and valine amino acids in the range of 2.00% to 5.00% by weight of said dry composition for providing energy during exercise and for repairing muscle cell damage after exercise.

2. A nutritional composition in a accordance with claim 1,
   a) wherein said one or more carbohydrates being sugars in the range of 70.00% to 82.00% by weight of said dry composition for providing energy during exercise; wherein said one or more carbohydrates are high glycemic sugars in the range of 60.00% to 65.00% by weight of said dry composition; and wherein said one or more carbohydrates are low glycemic sugars in the range of 9.00% to 15.00% by weight of said dry composition;
   b) wherein said one or more proteins being in the range of 19.00% to 21.00% by weight of said dry composition for stimulating the release of insulin to the muscle cells during exercise and for repairing muscle cells after exercise;
   c) wherein said first amino acid being glutamine in the range of 1.00% to 1.95% by weight of said dry composition for reducing muscle stress by stimulating the immune system during exercise and for stimulating muscle cell recovery after exercise;
   d) wherein said second amino acid being arginine in the range of 1.75% to 2.50% by weight of said dry composition for stimulating the release of insulin within the muscle cells in order to facilitate the transport of glucose into the muscle cells during exercise and for the synthesis of glucose into glycogen;
   e) wherein said first vitamin compound being vitamin C in the range of 0.60% to 1.00% by weight of said dry composition for use as an anti-oxidant for preventing free radical formation during exercise and for protecting muscle cell integrity during exercise;

f) wherein said second vitamin compound being vitamin E in the range of 0.80% to 1.05% by weight of said dry composition for use as an anti-oxidant for preventing free radical formation during exercise and for protecting muscle cell integrity during exercise;

g) wherein said first electrolyte ion being sodium (Na$^+$) compounds in the range of 0.50% to 1.00% by weight of said dry composition for replenishing electrolytes lost during exercise and for facilitating intestinal reabsorption of fluids;

h) wherein said second electrolyte ion being potassium (K$^+$) compounds in the range of 0.14% to 1.50% by weight of said dry composition for replenishing electrolytes lost during exercise and for facilitating intestinal reabsorption of fluids;

i) wherein said third electrolyte ion being magnesium (Mg$^+$) compounds in the range of 0.50% to 1.50% by weight of said dry composition for replenishing electrolytes lost during exercise and for facilitating energy dependent processes;

j) wherein said herbal compound being ciwujia in the range of 0.80% to 2.00% by weight of said dry composition for enhancing the immune system, reducing muscle stress, and decreasing heart rate during exercise; and k) wherein said one or more branched-chain amino acids consisting of leucine, isoleucine, and valine amino acids in the range of 3.00% to 4.00% by weight of said dry composition for providing energy during exercise and for repairing muscle cell damage after exercise.

3. A nutritional composition in accordance with claim 1, further including a flavor component for imparting a characteristic taste to said nutritional composition selected from the group consisting of water soluble natural or artificial extracts that include apple, banana, cherry, cinnamon, cranberry, grape, honeydew, honey, kiwi, lemon, lime, orange, peach, peppermint, pineapple, raspberry, tangerine, watermelon, wild cherry and equivalents thereof; being in the overall range of 0.10% to 2.0% by weight of said dry composition.

4. A nutritional composition in accordance with claim 1, further including a colorant component for imparting a characteristic color to said nutritional composition selected from the group consisting of water soluble natural or artificial dyes of blue, green, orange, red, violet, and yellow; iron oxide dyes, ultramarine pigments of blue, pink, red, and violet; and equivalents thereof; being in the overall range of 0.10% to 2.0% by weight of said dry composition.

5. A nutritional composition in accordance with claim 1, wherein said high glycemic sugars are selected from the group consisting of aldohexoses, disaccharides and polysaccharides such sugars being glucose, glucose polymers, dextrose, maltose, maltodextrins, maltotriose, lactose, galactose, sucrose, corn syrup, high fructose corn syrup, honey, maple syrup, molasses, beet sugar, cane sugar, and sucanat.

6. A nutritional composition in accordance with claim 1, wherein said low glycemic sugars are selected from the group consisting of ketohexoses such sugars being arabinose, ribose, xylose, fructose, levulose, psicose, sorbose, tagatose and sorbitol.

7. A nutritional composition in accordance with claim 1, wherein said proteins are selected from the group consisting of calcium caseinate, whey protein concentrate, whey protein isolate, soy protein, meat protein concentrate and yeast concentrate.

8. A nutritional composition in accordance with claim 1, wherein said sodium (Na$^+$) compounds are selected from the group consisting of sodium chloride, sodium acetate, acidic sodium citrate, acidic sodium phosphate, sodium amino salicylate, sodium bicarbonate, sodium bromide, sodium citrate, sodium lactate, sodium phosphate, sodium salicylate, anhydrous sodium sulphate, sodium sulphate, sodium tartrate, sodium benzoate, sodium selenite, sodium molybdate and combinations thereof.

9. A nutritional composition in accordance with claim 1, wherein said potassium (K$^+$) compounds are selected from the group consisting of potassium chloride, potassium acetate, potassium bicarbonate, potassium bromide, potassium citrate, potassium-D-gluconate, monobasic potassium phosphate, potassium tartrate, potassium sorbate and potassium iodide and combinations thereof.

10. A nutritional composition in accordance with claim 1, wherein said magnesium (Mg$^{+2}$) compounds are selected from the group consisting of magnesium chloride, magnesium oxide, magnesium sulphate, magnesium carbonate, magnesium aspartate and magnesium silicate and combinations thereof.

11. A nutritional composition in accordance with claim 1, wherein said herbal compound further includes ginseng, astralagus and cordyceps.

12. A nutritional composition in a liquid drink form for optimizing muscle performance during exercise and for enhancing muscle cell repair and recovery following the cessation of exercise, comprising:

a) one or more carbohydrates being sugars in the range of 11.00% to 15.00% by weight of said liquid composition for providing energy during exercise; wherein said one or more carbohydrates are high glycemic sugars in the range of 7.00% to 14.00% by weight of said liquid composition and wherein said one or more carbohydrates are low glycemic sugars in the range of 1.50% to 3.50% by weight of said liquid composition;

b) one or more proteins being in the range of 3.00% to 4.00% by weight of said liquid composition for stimulating the release of insulin to the muscle cells during exercise and for repairing muscle cells after exercise;

c) a first amino acid being glutamine in the range of 0.08% to 0.40% by weight of said liquid composition for reducing muscle stress by stimulating the immune system and for stimulating muscle cell recovery after exercise;

d) a second amino acid being arginine in the range of 0.20% to 0.60% by weight of said liquid composition for stimulating the release of insulin within the muscle cells in order to facilitate the transport of glucose into the muscle cells during exercise and for the synthesis of glucose into glycogen;

e) a first vitamin compound being vitamin C in the range of 0.05% to 0.60% by weight of said liquid composition for use as an anti-oxidant for preventing free radical formation during exercise and for protecting muscle cell integrity during exercise;

f) a second vitamin compound being vitamin E in the range of 0.10% to 0.60% by weight of said liquid composition for use as an anti-oxidant for preventing free radical formation during exercise and for protecting muscle cell integrity during exercise;

g) a first electrolyte ion being sodium (Na$^+$) compounds in the range of 0.05% to 0.60% by weight of said liquid composition for replenishing electrolytes lost during exercise and for facilitating intestinal reabsorption of fluids;

h) a second electrolyte ion being potassium (K$^+$) compounds in the range of 0.005% to 0.60% by weight of said liquid composition for replenishing electrolytes lost during exercise and for facilitating intestinal reabsorption of fluids;

i) a third electrolyte ion being magnesium (Mg$^{+2}$) compounds in the range of 0.05% to 0.60% by weight of said liquid composition for replenishing electrolytes lost during exercise and for facilitating energy dependent processes;

j) an herbal compound being ciwujia in the range of 0.005% to 0.60% by weight of said liquid composition for enhancing the immune system, reducing muscle stress, and decreasing heart rate during exercise; and k) one or more branched-chain amino acids consisting of leucine, isoleucine, and valine amino acids in the range of 0.40% to 0.90% by weight of said liquid composition for providing energy during exercise and for repairing muscle cell damage after exercise; and l) a diluent in the form of water or juice in the range of 80.00% to 85.00% by weight of said liquid composition for providing a liquid carrier to the dry powder of said nutritional composition.

13. A nutritional composition in accordance with claim 12, a) wherein said one or more carbohydrates being sugars is in the range of 12.00% to 14.00% by weight of said liquid composition for providing energy during exercise; wherein said one or more carbohydrates are high glycemic sugars in the range of 10.00% to 12.00% by weight of said liquid composition; and wherein said one or more carbohydrates are low glycemic sugars in the range of 1.65% to 2.50% by weight of said liquid composition;

b) wherein said one or more proteins being in the range of 3.65% to 3.85% by weight of said liquid composition for stimulating the release of insulin to the muscle cells during exercise and for repairing muscle cells after exercise;

c) wherein said first amino acid being glutamine in the range of 0.10% to 0.35% by weight of said liquid composition for reducing muscle stress by stimulating the immune system and for stimulating muscle cell recovery after exercise;

d) wherein said second amino acid being arginine in the range of 0.30% to 0.45% by weight of said dry composition for stimulating the release of insulin within the muscle cells in order to facilitate the transport of glucose into the muscle cells during exercise and for the synthesis of glucose into glycogen;

e) wherein said first vitamin compound being vitamin C in the range of 0.10% to 0.45% by weight of said liquid composition for use as an anti-oxidant for preventing free radical formation during exercise and for protecting muscle cell integrity during exercise;

f) wherein said second vitamin compound being vitamin E in the range of 0.10% to 0.40% by weight of said liquid composition for use as an anti-oxidant for preventing free radical formation during exercise and for protecting muscle cell integrity during exercise;

g) wherein said first electrolyte ion being sodium (Na$^+$) compounds in the range of 0.10% to 0.40% by weight of said liquid composition for replenishing electrolytes lost during exercise and for facilitating intestinal reabsorption of fluids;

h) wherein said second electrolyte ion being potassium (K$^+$) compounds in the range of 0.02% to 0.40% by weight of said liquid composition for replenishing electrolytes lost during exercise and for facilitating intestinal reabsorption of fluids;

i) wherein said third electrolyte ion being magnesium (Mg$^+$) compounds in the range of 0.09% to 0.40% by weight of said liquid composition for replenishing electrolytes lost during exercise and for facilitating energy dependent processes;

j) wherein said herbal compound being ciwujia in the range of 0.14% to 0.40% by weight of said liquid composition for enhancing the immune system, reducing muscle stress, and decreasing heart rate during exercise;

k) wherein said one or more branched-chain amino acids consisting of leucine, isoleucine, and valine amino acids in the range of 0.60% to 0.75% by weight of said liquid composition for providing energy during exercise and for repairing muscle cell damage after exercise; and l) wherein said diluent in the form of water or juice is in the range of 82.00% to 84.00% by weight of said liquid composition for providing a liquid carrier to the dry powder of said nutritional composition.

14. A nutritional composition in accordance with claim 12, further including a flavor component for imparting a characteristic taste to said nutritional composition selected from the group consisting of water soluble natural or artificial extracts that include apple, banana, cherry, cinnamon, cranberry, grape, honeydew, honey, kiwi, lemon, lime, orange, peach, peppermint, pineapple, raspberry, tangerine, watermelon, wild cherry and equivalents thereof; being in the overall range of 0.01% to 0.5% by weight of said liquid composition.

15. A nutritional composition in accordance with claim 12, further including a colorant component for imparting a characteristic color to said nutritional composition selected from the group consisting of water soluble natural or artificial dyes of blue, green, orange, red, violet, and yellow; iron oxide dyes, ultramarine pigments of blue, pink, red, and violet; and equivalents thereof; being in the overall range of 0.01% to 0.5% by weight of said liquid composition.

16. A nutritional composition in accordance with claim 12, wherein said high glycemic sugars are selected from the group consisting of aldohexoses, disaccharides and polysaccharides such sugars being glucose, glucose polymers, dextrose, maltose, maltodextrins, maltotriose, lactose, galactose, sucrose, corn syrup, high fructose corn syrup, honey, maple syrup, molasses, beet sugar, cane sugar, and sucanat.

17. A nutritional composition in accordance with claim 12, wherein said low glycemic sugars are selected from the group consisting of ketohexoses such sugars being arabinose, ribose, xylose, fructose, levulose, psicose, sorbose, tagatose and sorbitol.

18. A nutritional composition in accordance with claim 12, wherein said proteins are selected from the group consisting of calcium caseinate, casein hydrolyzate, whey protein concentrate, whey protein isolate, soy protein, meat protein concentrate and yeast concentrate.

19. A nutritional composition in accordance with claim 12, wherein said sodium (Na$^+$) compounds are selected from the group consisting of sodium chloride, sodium acetate, acidic sodium citrate, acidic sodium phosphate, sodium amino salicylate, sodium bicarbonate, sodium bromide, sodium citrate, sodium lactate, sodium phosphate, sodium salicylate, anhydrous sodium sulphate, sodium sulphate, sodium tartrate, sodium benzoate, sodium selenite and sodium molybdate.

20. A nutritional composition in accordance with claim 12, wherein said potassium ($K^+$) compounds are selected from the group consisting of potassium chloride, potassium acetate, potassium bicarbonate, potassium bromide, potassium citrate, potassium-D-gluconate, monobasic potassium phosphate, potassium tartrate, potassium sorbate and potassium iodide and combinations thereof.

21. A nutritional composition in accordance with claim 12, wherein said magnesium ($Mg^{+2}$) compounds are selected from the group consisting of magnesium chloride, magnesium oxide, magnesium sulphate, magnesium carbonate, magnesium aspartate and magnesium silicate and combinations thereof.

22. A nutritional composition in accordance with claim 12, wherein said first vitamin compound further includes vitamin B12 or beta-carotene for use as an anti-oxidant.

23. A nutritional composition in accordance with claim 12, wherein said herbal compound further includes ginseng, astralagus and cordyceps.

24. A nutritional composition in a dry powder form for optimizing muscle performance during exercise and for enhancing muscle cell repair and recovery following the cessation of exercise, comprising:
  a) carbohydrates and proteins in a ratio in the range of 2.8 to 4.2 parts of said carbohydrates to 1.0 part of said proteins; said carbohydrates for providing energy during exercise and said proteins for stimulating the release of insulin to the muscle cells during exercise and for repairing muscle cells after exercise;
  b) glutamine for reducing muscle stress by stimulating the immune system and for stimulating muscle cell recovery after exercise;
  c) arginine for stimulating the release of insulin within the muscle cells in order to facilitate the transport of glucose into the muscle cells during exercise and for the synthesis of glucose into glycogen;
  d) vitamin C for use as an anti-oxidant for preventing free radical formation during exercise and for protecting muscle cell integrity during exercise;
  e) vitamin E for use as an anti-oxidant for preventing free radical formation during exercise and for protecting muscle cell integrity during exercise;
  f) one or more electrolytes for replenishing electrolytes lost during exercise and for facilitating intestinal reabsorption of fluids, and for facilitating energy dependent processes;
  g) an herbal compound being ciwujia for enhancing the immune system, reducing muscle stress, and decreasing heart rate during exercise; and
  h) one or more branched-chain amino acids for providing energy during exercise and for repairing muscle cell damage after exercise.

25. A nutritional composition in accordance with claim 24, wherein said carbohydrates are sugars in the range of 68.00% to 88.00% by weight of said dry composition; wherein said carbohydrates are high glycemic sugars in the range of 50.00% to 70.0% by weight of said dry composition and wherein said carbohydrates are low glycemic sugars in the range of 8.00% to 20.00% by weight of said dry composition.

26. A nutritional composition in accordance with claim 25, wherein said high glycemic sugars are selected from the group consisting of aldohexoses, disaccharides and polysaccharides such sugars being glucose, glucose polymers, dextrose, maltose, maltodextrins, maltotriose, lactose, galactose, sucrose, corn syrup, high fructose corn syrup, honey, maple syrup, molasses, beet sugar, cane sugar, and sucanat.

27. A nutritional composition in accordance with claim 25, wherein said low glycemic sugars are selected from the group consisting of ketohexoses such sugars being arabinose, ribose, xylose, fructose, levulose, psicose, sorbose, tagatose and sorbitol.

28. A nutritional composition in accordance with claim 24, wherein said proteins are in the range of 17.00% to 22.00% by weight of said dry composition.

29. A nutritional composition in accordance with claim 28, wherein said proteins are selected from the group consisting of calcium caseinate, whey protein concentrate, whey protein isolate, soy protein, meat protein concentrate and yeast concentrate.

30. A nutritional composition in accordance with claim 24, wherein said glutamine is in the range of 0.05% to 2.00% by weight of said dry composition.

31. A nutritional composition in accordance with claim 24, wherein said arginine is in the range of 1.00% to 3.00% by weight of said dry composition.

32. A nutritional composition in accordance with claim 24, wherein said vitamin C is in the range of 0.50% to 2.00% by weight of said dry composition.

33. A nutritional composition in accordance with claim 24, wherein said vitamin E is in the range of 0.50% to 2.00% by weight of said dry composition.

34. A nutritional composition in accordance with claim 24, wherein said one or more electrolytes being a sodium ($Na^+$) compound, a potassium ($K^+$) compound and a magnesium ($Mg^{+2}$) compound are in the range of 0.10% to 2.00% by weight of said dry composition.

35. A nutritional composition in accordance with claim 34, wherein said sodium ($Na^+$) compounds are selected from the group consisting of sodium chloride, sodium acetate, acidic sodium citrate, acidic sodium phosphate, sodium amino salicylate, sodium bicarbonate, sodium bromide, sodium citrate, sodium lactate, sodium phosphate, sodium salicylate, anhydrous sodium sulphate, sodium sulphate, sodium tartrate, sodium benzoate, sodium selenite and sodium molybdate.

36. A nutritional composition in accordance with claim 34, wherein said potassium ($K^+$) compounds are selected from the group consisting of potassium chloride, potassium acetate, potassium bicarbonate, potassium bromide, potassium citrate, potassium-D-gluconate, monobasic potassium phosphate, potassium tartrate, potassium sorbate and potassium iodide and combinations thereof.

37. A nutritional composition in accordance with claim 34, wherein said magnesium ($Mg^{+2}$) compounds are selected from the group consisting of magnesium chloride, magnesium oxide, magnesium sulphate, magnesium carbonate, magnesium aspartate and magnesium silicate and combinations thereof.

38. A nutritional composition in accordance with claim 24, wherein said ciwujia is in the range of 0.50% to 3.00% by weight of said dry composition.

39. A nutritional composition in accordance with claim 24, wherein said one or more branched-chain amino acids being leucine, isoleucine and valine are in the range of 2.00% to 5.00% by weight of said dry composition.

40. A nutritional composition in accordance with claim 24, further including a flavor component for imparting a characteristic taste to said nutritional composition selected from the group consisting of water soluble natural or artificial extracts that include apple, banana, cherry, cinnamon, cranberry, grape, honeydew, honey, kiwi, lemon, lime, orange, peach, peppermint, pineapple, raspberry, tangerine, watermelon, wild cherry and equivalents thereof; being in the overall range of 0.10% to 2.0% by weight of said dry composition.

41. A nutritional composition in accordance with claim 24, further including a colorant component for imparting a characteristic color to said nutritional composition selected from the group consisting of water soluble natural or artificial dyes of blue, green, orange, red, violet, and yellow; iron oxide dyes, ultramarine pigments of blue, pink, red, and violet; and equivalents thereof; being in the overall range of 0.10% to 2.0% by weight of said dry composition.

42. A nutritional composition in a liquid drink form for optimizing muscle performance during exercise and for enhancing muscle cell repair and recovery following the cessation of exercise, comprising:
   a) carbohydrates and proteins in a ratio in the range of 2.8 to 4.2 parts of said carbohydrates to 1.0 part of said proteins; said carbohydrates for providing energy during exercise and said proteins for stimulating the release of insulin to the muscle cells during exercise and for repairing muscle cells after exercise;
   b) glutamine for reducing muscle stress by stimulating the immune system and for stimulating muscle cell recovery after exercise;
   c) arginine for stimulating the release of insulin within the muscle cells in order to facilitate the transport of glucose into the muscle cells during exercise and for the synthesis of glucose into glycogen;
   d) vitamin C for use as an anti-oxidant for preventing free radical formation during exercise and for protecting muscle cell integrity during exercise;
   e) vitamin E for use as an anti-oxidant for preventing free radical formation during exercise and for protecting muscle cell integrity during exercise;
   f) one or more electrolytes for replenishing electrolytes lost during exercise and for facilitating intestinal reabsorption of fluids, and for facilitating energy dependent processes;
   g) an herbal compound being ciwujia for enhancing the immune system, reducing muscle stress, and decreasing heart rate during exercise;
   h) one or more branched-chain amino acids for providing energy during exercise and for repairing muscle cell damage after exercise; and
   i) a diluent in the form of water or juice for providing a liquid carrier to the dry powder of said nutritional composition.

43. A nutritional composition in accordance with claim 42, wherein said carbohydrates are sugars in the range of 11.00% to 15.00% by weight of said liquid composition; wherein said carbohydrates are high glycemic sugars in the range of 7.00% to 14.00% by weight of said liquid composition; and wherein said carbohydrates are low glycemic sugars in the range of 1.50% to 3.50% by weight of said liquid composition.

44. A nutritional composition in accordance with claim 43, wherein said high glycemic sugars are selected from the group consisting of aldohexoses, disaccharides and polysaccharides such sugars being glucose, glucose polymers, dextrose, maltose, maltodextrins, maltotriose, lactose, galactose, sucrose, corn syrup, high fructose corn syrup, honey, maple syrup, molasses, beet sugar, cane sugar, and sucanat.

45. A nutritional composition in accordance with claim 43, wherein said low glycemic sugars are selected from the group consisting of ketohexoses such sugars being arabinose, ribose, xylose, fructose, levulose, psicose, sorbose, tagatose and sorbitol.

46. A nutritional composition in accordance with claim 42, wherein said proteins are in the range of 3.00% to 4.00% by weight of said liquid composition.

47. A nutritional composition in accordance with claim 46, wherein said proteins are selected from the group consisting of calcium caseinate, whey protein concentrate, whey protein isolate, soy protein, meat protein concentrate and yeast concentrate.

48. A nutritional composition in accordance with claim 42, wherein said glutamine is in the range of 0.08% to 0.40% by weight of said liquid composition.

49. A nutritional composition in accordance with claim 42, wherein said arginine is in the range of 0.20% to 0.60% by weight of said liquid composition.

50. A nutritional composition in accordance with claim 42, wherein said vitamin C is in the range of 0.05% to 0.60% by weight of said liquid composition.

51. A nutritional composition in accordance with claim 42, wherein said Vitamin E is in the range of 0.10% to 0.60% by weight of said liquid composition.

52. A nutritional composition in accordance with claim 42, wherein said one or more electrolytes being a sodium ($Na^+$) compound, a potassium ($K^+$) compound, and a magnesium ($Mg^{+2}$) compound are in the range of 0.005% to 0.5% by weight of said liquid compound.

53. A nutritional composition in accordance with claim 52, wherein said sodium ($Na^+$) compounds are selected from the group consisting of sodium chloride, sodium acetate, acidic sodium citrate, acidic sodium phosphate, sodium amino salicylate, sodium bicarbonate, sodium bromide, sodium citrate, sodium lactate, sodium phosphate, sodium salicylate, anhydrous sodium sulphate, sodium sulphate, sodium tartrate, sodium benzoate, sodium selenite and sodium molybdate and combinations thereof.

54. A nutritional composition in accordance with claim 52, wherein said potassium ($K^+$) compounds are selected from the group consisting of potassium chloride, potassium acetate, potassium bicarbonate, potassium bromide, potassium citrate, potassium-D-gluconate, monobasic potassium phosphate, potassium tartrate, potassium sorbate and potassium iodide and combinations thereof.

55. A nutritional composition in accordance with claim 52, wherein said magnesium ($Mg^{+2}$) compounds are selected from the group consisting of magnesium chloride, magnesium oxide, magnesium sulphate, magnesium carbonate, magnesium aspartate and magnesium silicate and combinations thereof.

56. A nutritional composition in accordance with claim 42, wherein said ciwujia is in the range of 0.14% to 0.40% by weight of said liquid composition.

57. A nutritional composition in accordance with claim 42, wherein said one or more branched-chain amino acids being leucine, isoleucine and valine are in the range of 0.60% to 0.75% by weight of liquid composition.

58. A nutritional composition in accordance with claim 42, further including a flavor component for imparting a characteristic taste to said nutritional composition selected from the group consisting of water soluble natural or artificial extracts that include apple, banana, cherry, cinnamon, cranberry, grape, honeydew, honey, kiwi, lemon, lime, orange, peach, peppermint, pineapple, raspberry, tangerine, watermelon, wild cherry and equivalents thereof; being in the overall range of 0.01% to 0.5% by weight of said liquid composition.

59. A nutritional composition in accordance with claim 42, further including a colorant component for imparting a characteristic color to said nutritional composition selected from the group consisting of water soluble natural or artificial dyes of blue, green, orange, red, violet, and yellow; iron oxide dyes, ultramarine pigments of blue, pink, red, and violet; and equivalents thereof; being in the overall range of 0.01% to 0.5% by weight of said liquid composition.

60. A nutritional composition in an energy bar form for optimizing muscle performance during exercise and for enhancing muscle cell repair and recovery following the cessation of exercise, comprising:
   a) carbohydrates and proteins in a ratio in the range of 2.8 to 4.2 parts of said carbohydrates to 1.0 part of said proteins; said carbohydrates for providing energy during exercise and said proteins for stimulating the release of insulin to the muscle cells during exercise and for repairing muscle cells after exercise;
   b) glutamine for reducing muscle stress by stimulating the immune system and for stimulating muscle cell recovery after exercise;
   c) arginine for stimulating the release of insulin within the muscle cells in order to facilitate the transport of glucose into the muscle cells during exercise and for the synthesis of glucose into glycogen;
   d) vitamin C for use as an anti-oxidant for preventing free radical formation during exercise and for protecting muscle cell integrity during exercise;
   e) vitamin E for use as an anti-oxidant for preventing free radical formation during exercise and for protecting muscle cell integrity during exercise;
   f) one or more electrolytes for replenishing electrolytes lost during exercise and for facilitating intestinal reabsorption of fluids, and for facilitating energy dependent processes;
   g) an herbal compound being ciwujia for enhancing the immune system, reducing muscle stress, and decreasing heart rate during exercise;
   h) one or more branched-chain amino acids for providing energy during exercise and for repairing muscle cell damage after exercise; and
   i) a carrier in the form of chocolate, oats, wheat, peanut butter, semi-dried fruits, grains and combinations thereof for providing a semi-liquid carrier to the dry powder of said nutritional composition.

61. A nutritional composition in a gelatin form for optimizing muscle performance during exercise and for enhancing muscle cell repair and recovery following the cessation of exercise, comprising:
   a) carbohydrates and proteins in a ratio in the range of 2.8 to 4.2 parts of said carbohydrates to 1.0 part of said proteins; said carbohydrates for providing energy during exercise and said proteins for stimulating the release of insulin to the muscle cells during exercise and for repairing muscle cells after exercise;
   b) glutamine for reducing muscle stress by stimulating the immune system and for stimulating muscle cell recovery after exercise;
   c) arginine for stimulating the release of insulin within the muscle cells in order to facilitate the transport of glucose into the muscle cells during exercise and for the synthesis of glucose into glycogen;
   d) vitamin C for use as an anti-oxidant for preventing free radical formation during exercise and for protecting muscle cell integrity during exercise;
   e) vitamin E for use as an anti-oxidant for preventing free radical formation during exercise and for protecting muscle cell integrity during exercise;
   f) one or more electrolytes for replenishing electrolytes lost during exercise and for facilitating intestinal reabsorption of fluids, and for facilitating energy dependent processes;
   g) an herbal compound being ciwujia for enhancing the immune system, reducing muscle stress, and decreasing heart rate during exercise;
   h) one or more branched-chain amino acids for providing energy during exercise and for repairing muscle cell damage after exercise; and
   i) a diluent in the form of water or juice and gelatin for providing a liquid carrier to the dry powder of said nutritional composition.

62. A nutritional composition in a liquid drink form for optimizing muscle performance during exercise and for enhancing muscle cell repair and recovery following the cessation of exercise, comprising:
   a) one or more carbohydrates being sugars in the range of 11.00% to 15.00% by weight of said liquid composition for providing energy during exercise; wherein said one or more carbohydrates are high glycemic sugars in the range of 7.00% to 14.00% by weight of said liquid composition; and wherein said one or more carbohydrates are low glycemic sugars in the range of 1.50% to 3.50% by weight of said liquid composition;
   b) one or more proteins being in the range of 3.00% to 4.00% by weight of said liquid composition for stimulating the release of insulin to the muscle cells during exercise and for repairing muscle cells after exercise;
   c) one or more amino acids in the range of 0.08% to 0.40% by weight of said liquid composition for reducing muscle stress, for stimulating muscle cell recovery after exercise, and for stimulating the release of insulin within the muscle cells in order to facilitate the transport of glucose into the muscle cells during exercise and for the synthesis of glucose into glycogen;
   d) one or more vitamin compounds in the range of 0.05% to 0.60% by weight of said liquid composition for use as an anti-oxidant for preventing free radical formation during exercise;
   e) one or more electrolyte compounds in the range of 0.005% to 0.60% by weight of said liquid composition for replenishing electrolytes lost during exercise and for facilitating intestinal reabsorption of fluids; and for facilitating energy dependent processes;
   f) an herbal compound in the range of 0.005% to 0.60% by weight of said liquid composition for enhancing the immune system, reducing muscle stress, and decreasing heart rate during exercise;
   g) one or more branched-chain amino acids in the range of 0.004% to 0.90% by weight of said liquid composition for providing energy during exercise and for repairing muscle cell damage after exercise; and
   h) a diluent in the range of 80.00% to 85.00% by weight of said liquid composition for providing a liquid carrier for the dry powder of said nutritional composition.

63. A nutritional composition in accordance with claim 62, further including a flavor component for imparting a characteristic taste to said nutritional composition selected from the group consisting of water soluble natural or artificial extracts that include apple, banana, cherry, cinnamon, cranberry, grape, honeydew, honey, kiwi, lemon, lime, orange, peach, peppermint, pineapple, raspberry, tangerine, watermelon, wild cherry and equivalents thereof; being in the overall range of 0.01% to 0.5% by weight of said liquid composition.

64. A nutritional composition in accordance with claim 62, further including a colorant component for imparting a characteristic color to said nutritional composition selected from the group consisting of water soluble natural or artificial dyes of blue, green, orange, red, violet, and yellow; iron oxide dyes, ultramarine pigments of blue, pink, red, and violet; and equivalents thereof; being in the overall range of 0.01% to 0.5% by weight of said liquid composition.

65. A nutritional composition in accordance with claim 62, wherein said high glycemic sugars are selected from the group consisting of glucose, glucose polymers, dextrose, maltose, maltodextrins, maltotriose, lactose, galactose, sucrose, corn syrup, high fructose corn syrup, honey, maple syrup, molasses, beet sugar, cane sugar, and sucanat.

66. A nutritional composition in accordance with claim 62, wherein said low glycemic sugars are selected from the group consisting of ketohexoses such sugars being arabinose, ribose, xylose, fructose, levulose, psicose, sorbose, tagatose and sorbitol.

67. A nutritional composition in accordance with claim 62, wherein said proteins are selected from the group consisting of calcium caseinate, whey protein concentrate, whey protein isolate, soy protein, meat protein concentrate and yeast concentrate.

68. A nutritional composition in accordance with claim 62, wherein said amino acids are glutamine and arginine.

69. A nutritional composition in accordance with claim 62, wherein said vitamin compounds are Vitamin C, Vitamin E, Vitamin B12 and beta-carotene.

70. A nutritional composition in accordance with claim 62, wherein said electrolyte compounds are sodium ($Na^+$) compounds, potassium ($K^+$) compounds and magnesium ($Mg^{+2}$) compounds.

71. A nutritional composition in accordance with claim 70, wherein said sodium ($Na^+$) compounds are selected from the group consisting of sodium chloride, sodium acetate, acidic sodium citrate, acidic sodium phosphate, sodium amino salicylate, sodium bicarbonate, sodium bromide, sodium citrate, sodium lactate, sodium phosphate, sodium salicylate, anhydrous sodium sulphate, sodium sulphate, sodium tartrate, sodium benzoate, sodium selenite and sodium molybdate and combinations thereof.

72. A nutritional composition in accordance with claim 70, wherein said potassium ($K^+$) compounds are selected from the group consisting of potassium chloride, potassium acetate, potassium bicarbonate, potassium bromide, potassium citrate, potassium-D-gluconate, monobasic potassium phosphate, potassium tartrate, potassium sorbate and potassium iodide and combinations thereof.

73. A nutritional composition in accordance with claim 70, wherein said magnesium ($Mg^{+2}$) compounds are selected from the group consisting of magnesium chloride, magnesium oxide, magnesium sulphate, magnesium carbonate, magnesium aspartate and magnesium silicate and combinations thereof.

74. A nutritional composition in accordance with claim 62, wherein said herbal compound includes ciwujia, ginseng, astralagus and cordyceps.

75. A nutritional composition in accordance with claim 62, wherein said branched-chain amino acids are leucine, isoleucine and valine.

76. A nutritional composition in accordance with claim 62, wherein said diluent is in the form of water, juice or combinations thereof.

77. A nutritional composition in accordance with claim 76, wherein said juices are selected from the group consisting of grape juice, apple juice, cranberry juice, orange juice, grapefruit juice, tangerine juice, peach juice, strawberry juice and combinations and equivalents thereof.

* * * * *